United States Patent [19]
Hoeft

[11] Patent Number: 5,865,757
[45] Date of Patent: Feb. 2, 1999

[54] PROCESS AND A DEVICE FOR DETERMINING THE CEREBRAL BLOOD FLOW CBF, AND THE INTRACEREBRAL BLOOD VOLUME ICBV

[76] Inventor: Andreas Hoeft, Neissestrasse 6, D-53127 Bonn, Germany

[21] Appl. No.: 849,050

[22] PCT Filed: Nov. 29, 1995

[86] PCT No.: PCT/DE95/01690

§ 371 Date: May 29, 1997

§ 102(e) Date: May 29, 1997

[87] PCT Pub. No.: WO96/16594

PCT Pub. Date: Jun. 6, 1996

[30] Foreign Application Priority Data

Dec. 1, 1994 [DE] Germany .......................... 44 42 751.4

[51] Int. Cl.⁶ ..................................................... A61B 5/02
[52] U.S. Cl. ............................................ 600/504; 600/505
[58] Field of Search ................................... 600/504, 481, 600/505, 507, 485

[56] References Cited

PUBLICATIONS

"Measurement of Jugular Venous Flow by Thermal Dilution", Edwin M. Wilson et al., Institute of Electrical and Engineers (IEEE) proceeding of the 23rd Annual Conference on Engineering in Medicine and Biology, vol. 12, Nov. 16, 1970, New York, p. 276.

"Messung der Koronardurchblutung mit einem Doppelfiber–optiksystem und rechnergestützter Entfaltung von transkoronaren Farbstoffdilutionssignalen", (English : Measurement of Coronary Blood Flow by a Double Fiberoptic System with Microcomputer–Aided Deconvolution of Transconronary Dye Dilution Tracings), *Biomedizinische Technik*, Andreas Hoeft et al., vol. 28, No. 10, Oct. 1983, pp. 216–220.

"Thermal Recovery After Passage of the Pulmonary Circulation Assessed by Deconvulution", *Journal of Applied Physiology*, J. Böck et al., vol. 64, No. 3, Mar. 1988, pp. 1210–1216.

"Calculation of Body Transport Function", *Physics in Medicine and Biology*, T. Schröder et al., vol. 37, No. 11, Nov. 1992.

*Primary Examiner*—Max Hindenburg
*Assistant Examiner*—Bryan K. Yarnell
*Attorney, Agent, or Firm*—Burns, Doane, Swecker & Mathis, L.L.P.

[57] ABSTRACT

A process and a device for determining the cerebral blood flow, and the intracerebral blood volume are described.

After injection into the bloodstream of a predefined quantity of a double indicator, arterial and venous measurements of the indicator dilution curves resulting in the blood stream are carried out. A dye solution differing in its temperature from the body temperature serves as a double indicator, in which heat or cold constitute a highly diffusible indicator component, and dye, preferably indo cyanine green ICG, constitute an intravascular indicator component. The cerebral blood flow CBF is calculated from the ratio of a distribution coefficient $\lambda_{therm}$ of the highly diffusible indicator component therm between blood and cerebral tissue and the mean transit time $mtt_{therm}$ of the highly diffusible indicator component therm through the brain. The intracerebral blood volume ICBV is calculated from the product of cerebral blood flow CBF and the mean transit time $mtt_{ICG}$ of the intravascular indicator component ICG.

14 Claims, 2 Drawing Sheets

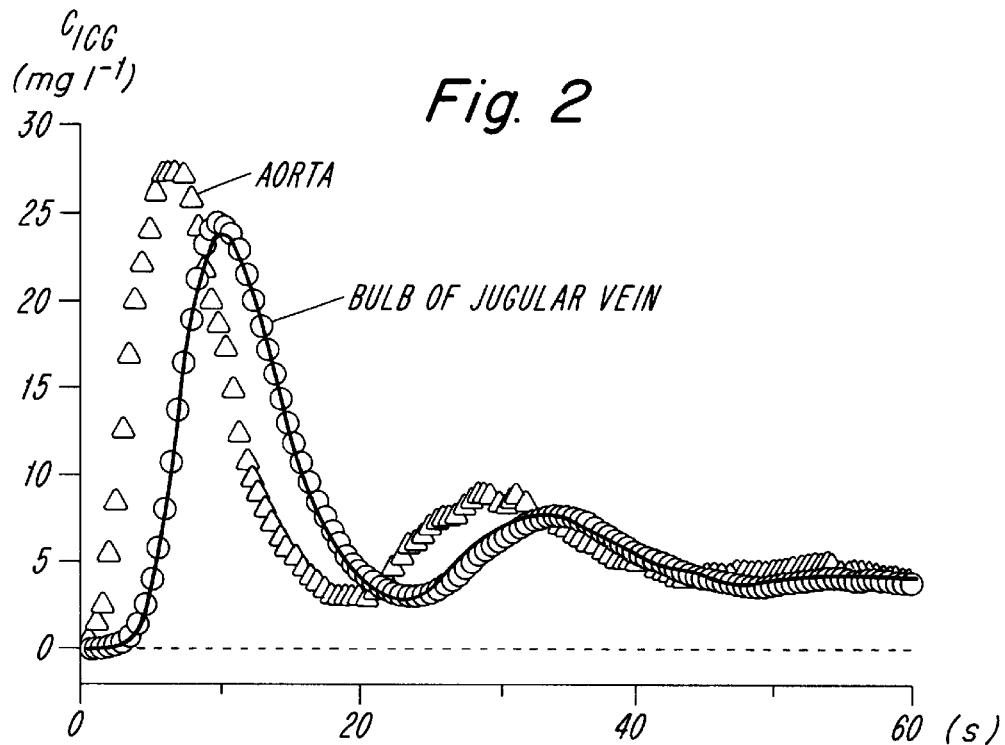
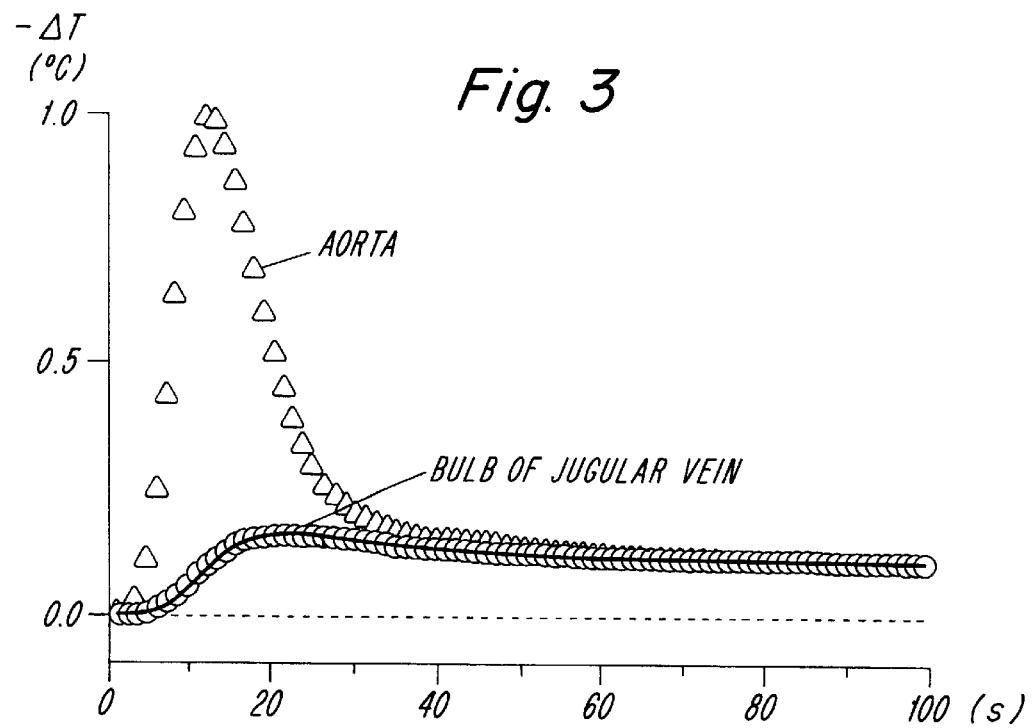

PROCESS AND A DEVICE FOR DETERMINING THE CEREBRAL BLOOD FLOW CBF, AND THE INTRACEREBRAL BLOOD VOLUME ICBV

BACKGROUND OF THE INVENTION

Adequate blood flow through the brain at all times is not only an unalterable prerequisite for normal cerebral function, but also an essential necessity for the survival of the individual in situations of impaired cardiocirculatory function. Even short-term interruptions of the cerebral blood flow can cause irreversible damage which either leads to loss of life or is followed by the most serious defective healing.

In medicine, monitoring of cerebral blood flow poses a particular problem in the case of unconscious patients, for example during general anaesthesia or with intensive-care patients on a respirator. In these patients, cerebral function must also be suppressed for reasons of pain avoidance, and thus there is no possibility of indirectly judging to what extent cerebral blood flow is adequate. The problem is particularly severe with patients suffering from cerebral diseases, such as for example the most severe cerebral concussion and cerebral tumour.

On the one hand in these cases, the brain tends to swell, whereby blood flow can be impeded. On the other hand, decoupling of cerebral blood flow from the metabolic requirements of the brain may occur whereby the accompanying expansion of blood vessels can cause cerebral swelling in itself. While in the one case therapeutic measures aiming at promoting cerebral blood flow would have to be undertaken, in the other case a reduction in cerebral blood flow would have to be aimed at.

It is therefore desirable to find not only a simple method, especially one that can be applied at the bedside, for measuring cerebral blood flow and intracerebral blood volume, but also one that offers simple monitoring for effectiveness and dosage rate when testing newly developed medicaments for promoting or reducing cerebral blood flow.

So far, only relatively expensive processes have been available for measuring cerebral blood flow in patients. As a rule, these are indicator dilution processes in which foreign gases are used as indicators. In a technique that has been used for a long time (Kety-Schmid technique) saturation of the blood and the brain with laughing gas or argon takes place, whereby the respective gas is enriched in the respiratory air. The analysis process takes place concurrently by means of several blood samples in the arterial and in the cerebrovenous blood for which firstly an arterial catheter and secondly a catheter in the "bulbus venae jugularis" is required. The latter is inserted retrogradely by way of a jugular vein (vena jugularis interna), to the level of the base of the skull.

With a different method, radioactively marked xenon is used which is injected as a bolus in aqueous solution. With this technique, gas indication is by means of extra cranial detectors. Due to their associated costs as well as due to the equipment required, both these methods are feasible during operations or with intensive-care patients only for scientific purposes; they are unsuitable for the demands of clinical routine. In the Kety-Schmid process, the blood samples must be processed through extensive laboratory analysis, so that the result is usually available only hours later. Apart from the high cost, the main disadvantage of the xenon technique is the associated radiation exposure for both patient and personnel.

From Journal of Applied Physiology, vol. 64, nr. 3, March 1988, pages 1210–1216, Bock et al.: "Thermal recovery after passage of pulmonary circulation assessed by deconvolution" it is known to determine the cardiac stroke volume and the extravascular thermal lung volume. To this effect, a double indicator of heat/cold on the one hand, and dye on the other hand, the quantity of which must be precisely known, is injected into the bloodstream. Thereafter, the indicator dilution curves are measured and subsequently the areas below the curves are determined. The ratio of indicator quantity to area below the curves subsequently reveals the blood flow in absolute units, e.g. in milliliters per minute.

The indicator heat/cold serves to determine the blood flow "cardiac stroke volume". The extravascular thermal lung volume is determined from the product of cardiac stroke volume and mean transit time, whereby the intravascular lung volume is deducted, in which the difference between mean transit time of the indicator heat/cold and the indicator dye is constituted.

SUMMARY OF THE INVENTION

It is the object of the present invention to design a process and a device for determining the cerebral blood flow and the intracerebral blood volume, which provides a simple, quick and accurate determination of these variables while at the same time causing the least possible physical impairment.

This object is achieved in a process according to the precharacterizing part of claim 1, by the characteristics stated in claim 1, and in a device according to the precharacterizing part of claim 8, by the characteristics of claim 8. Developments and advantageous embodiments are stated in the dependent claims.

The invention makes use of a double-indicator dilution process with a dye solution whose injection temperature differs from the body temperature, where heat or cold result in a highly diffusible indicator component and dye, preferably indo cyanine green ICG, constituting an intravascular indicator component. The different transport processes of the two indicator components offer the possibility to determine not only cerebral blood flow but also intracerebral blood volume.

Cerebral blood flow CBF is determined from the mean transit time of heat or cold through the brain $mtt_{therm}$, whereby the following relationship applies:

(1) $CBF = \lambda_{therm} / mtt_{therm}$

In this, the factor $\lambda_{therm}$ is the distribution coefficient of the indicator heat or cold between cerebral tissue and blood. It represents a natural constant which can be empirically determined either by one-off comparative measurements by means of other processes for determining cerebral blood flow, or calculated by way of the specific heat capacity of the cerebral substance.

The intracerebral blood volume ICBV is calculated from the product of the CBF and the mean transit time of the intravascular dye indicator ICG $mtt_{ICG}$:

(2) $ICBV = CBF \cdot mtt_{ICG}$

Administration of the double indicator is by bolus injection, preferably central-venously, by way of a respective catheter. Moreover, the arterial and cerebrovenous indicator dilution curves are measured. This can take place by means of combined fibre-optic thermistor catheters placed in the aorta by way of the arteria femoralis, and placed in the bulbus venae jugularis by way of the vena jugularis interna.

The mean transit times $mtt_{ICG}$, $mtt_{therm}$ can be determined from the transcerebral transport functions of the two indicator components $g_{therm}(t)$ or $g_{IGC}(t)$ respectively. A relationship generally applies to the transport functions $g(t)$, the arterial $a(t)$ and the cerebrovenous $v(t)$ indicator curves, with the said relationship being expressed by the following convolution integral:

$$v(t) = \int_0^\infty g(t-u)a(u)du \qquad (3)$$

The mean transit time corresponds to the first moment of the transport function:

$$mtt = \frac{\int_0^\infty g(t) \cdot t dt}{\int_0^\infty g(t) dt} \qquad (4)$$

If—as in this case—the arterial and venous indicator dilution curves are present as measurement signals, then the transport functions must be determined by "de-convolution" of $a(t)$ and $v(t)$. This can be carried out by model-free processes. It is however numerically more favourable to apply model functions. If the basic form of transport functions is known and describable by a function, e.g. by a logarithmic normal distribution, then, in respect of measured curve pairs of $a(t)$ and $v(t)$, the parameters of the respective transport functions, in particular the mean transit times, can be determined by an iterative, non-linear matching process. In this, the difference between measured cerebrovenous concentration and the convolution result of the arterial curve with the transport function is minimised according to the process of the smallest squares, by iterative variation of the parameters of the transport function $g(t)$ $$\left[v(t) - \int_0^\infty g(t-u)a(u)du\right]^2 = \min \qquad (5)$$

Logarithmic normal distributions have proven successful in describing intravascular dye-transport functions. In the case of the transcerebral double-indicator dilution, thus the following starting point can be selected in relation to $g(t)$:

$$g_{IGC}(t) = g_{log\,nor}(t, mtt, \sigma) = \frac{1}{\sqrt{2\pi\sigma t}} \cdot e^{-\frac{\left(\ln\frac{t}{mtt} + \frac{\sigma^2}{2}\right)^2}{2\sigma^2}} \qquad (6)$$

In the form stated here, which differs somewhat from the usual way of representing the logarithmic normal distribution, the function is shown in such a way that the mean transit time mtt and the relative dispersion σ directly constitute the parameters of the distribution.

It is possible that two intravascular compartments with differing rates of blood flow exist. In this case, the transport function can be represented by the sum of two normal distributions, whereby α constitutes the distribution factor:

$$g_{IGC}(t) = \alpha_{ICG} \cdot g_{log\,nor\,1}(t, mtt_1, \sigma_1) + \qquad (7)$$
$$+ (1-\alpha_{ICG}) \cdot g_{log\,nor\,2}(t, mtt_2, \sigma_2)$$

The transport process for the indicator component heat or cold can be divided into several sections:

1. Inward transport, predominantly intravascular, by way of the arterial vascular system, 2. Equilibration of the "highly diffusible" indicator heat or cold at the level of micro circulation, 3. Outbound transport of heat or cold by way of the venous vascular system. In each case, the transport process for each section can be described by one transport function $g_{art}(t)$, $g_{mikro}(t)$, $g_{ven}(t)$; the entire transport process then results from the convolution of the three transport functions:

$$g_{therm}(t) = g_{art}(t) * g_{mikro}(t) * g_{ven}(t) \qquad (8)$$

whereby the operator "*" corresponds to the convolution integral. Since the convolution is commutative, $g_{art}(t)$ and $g_{ven}(t)$ can be summarised as an intravascular transport function. This in turn is however identical with the intravascular transport function which can be determined by deconvolution of the dye curves. Thus, the following applies:

$$g_{therm}(t) = g_{ICG}(t) * g_{mikro}(t) \qquad (9)$$

In this way, determination of $g_{therm}(t)$ can occur more favourably even with limited signal-to-noise ratio, because in the case of known $g_{ICG}(t)$, merely the parameters of $g_{mikro}(t)$ have to be determined by deconvolution of the dye curves. Equilibration at the level of microcirculation is to be regarded as an almost ideal mixing process. Thus for the transport function an exponential course is to be arranged:

$$g_{mikro}(t) = mtt_{mikro}\, e^{-\frac{t}{mtt_{mikro}}} \qquad (10)$$

As a rule it has been observed that due to the grey and white matter there are two compartments in the brain with different rates of blood supply. Their total transport function can then be represented as the sum of two exponential functions, whereby α again is the distribution factor:

$$g_{mikro}(t) = a \cdot mtt_{mikro\,1}\, e^{-\frac{t}{mtt_{mikro\,1}}} + \qquad (11)$$
$$(1-a) \cdot mtt_{mikro\,2}\, e^{-\frac{t}{mtt_{mikro\,2}}}$$

BRIEF DESCRIPTION OF THE DRAWINGS

Below, the process and device are illustrated by way of a drawing, as follows:

FIG. 2 shows a typical arterial and cerebrovenous dye dilution curve; and

FIG. 3 shows a typical arterial and cerebrovenous thermal dilution curve.

DETAILED DESCRIPTION OF THE INVENTION

Figure 1:
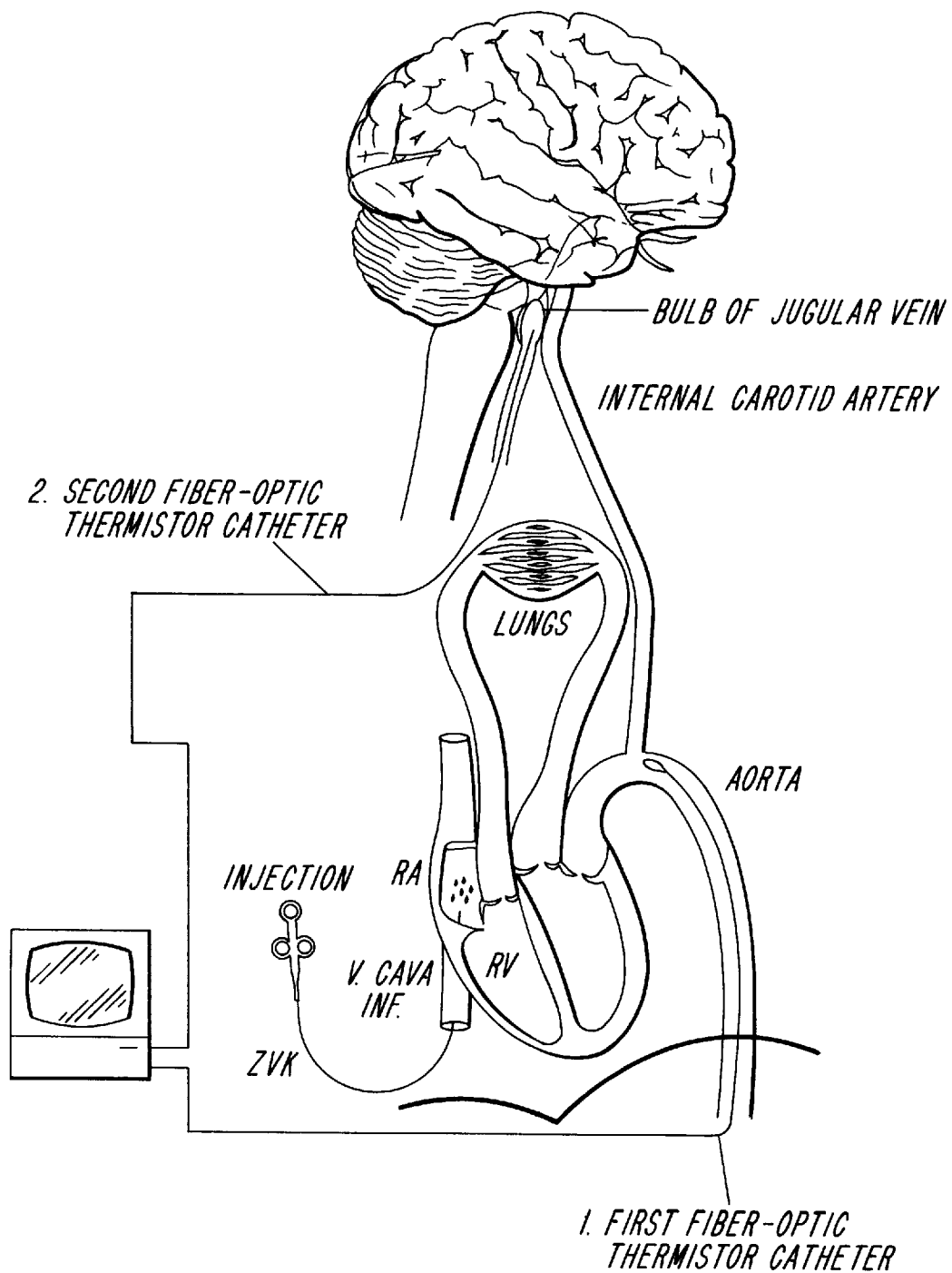
FIG. 1 shows a measuring apparatus with a scheme for catheter arrangement.

The measuring apparatus comprises two measuring sensors, each one being a combined fibre-optic thermistor catheter, linked to a computer for evaluation purposes. A first fibre-optic thermistor catheter is placed in the aorta, by insertion with a respective insertion instrument, into the arteria femoralis. A second fibre-optic thermistor catheter is placed in the venae jugularis which it reaches through retrograde catheterisation of the vena jugularis interna.

After venous bolus injection, for example by means of a central venous catheter CVC, of an adequate indicator quantity, e.g. 0.2–0.4 mg/kg ICG in 0.3–0.5 ml/kg ice-cold solution, the resulting indicator dilution curves are measured by means of the fibre-optic thermistor catheter and recorded by the computer. Measuring should be carried out over a time span of at least five minutes. During measuring, the indicator dilution curves shown in FIGS. 2 and 3 are obtained, this is to say the dye dilution curves according to FIG. 2 which shows a typically arterial (triangles) and cerebrovenous (empty circles) dye dilution curve following injection of a cold dye bolus (25 mg) into the right atrium; and the thermodilution curves according to FIG. 3 which shows a typical arterial (triangles) and cerebrovenous (empty circles) thermodilution curve following injection of a cold dye solution bolus (0.4 ml/kg 3° C.) into the right atrium.

During evaluation of the indicator dilution curves, first of all, calculation of the intravascular transport function $g_{ICG}(t)$ from the dye dilution curve takes place. For that, the values of the recorded arterial a(t) and cerebrovenous v(t) dye dilution curve according to FIG. 2 are put into equation (5). As a model function for g(t), the expression from equation (6) or, when taking into account two compartments, the modified expression from equation (7) is put in. Now, the parameters for the mean transit time mtt and the relative dispersion σ are varied until the difference between the measured cerebrovenous indicator curve v(t) and the convolution result of the measured arterial indicator curve a(t) is minimised according to equation (5). Thereafter, the mean transit time $mtt_{ICG}$ and the dye transport function $g_{ICG}(t)$ are known. The relative dispersion σ is not further evaluated here.

If the arterial dye curve according to FIG. 2 is convoluted with the dye transport function $g_{ICG}(t)$ obtained in this way, a curve very precisely matched to the cerebrovenous dye curve according to FIG. 2 results, as is shown by the solid line.

Subsequently, calculation of the diffusible transport function $g_{therm}(t)$ from the thermodilution curves takes place. To bring this about, the values of the recorded arterial a(t) and cerebral venous v(t) thermodilution curve according to FIG. 3 are put into equation (5). For $g_{ICG}(t)$ the expression from equation (9) is put in, whereby $g_{ICG}$ (t) is already known from the previous calculation, and for $g_{mikro}(t)$ the expression from equation (10) or, when taking into account two compartments, the modified expression from equation (11) is put in as a model function. Now the sole parameter for the mean transit time $mtt_{therm}$ is varied until the difference between the measured cerebrovenous indicator curve v(t) and the convolution result of the measured arterial indicator curve a(t) is minimised according to equation (5). Thereafter, the mean transit time $mtt_{therm}$ and the thermal transport function $g_{therm}(t)$ are known too.

If the arterial thermal dilution curve according to FIG. 3 is convoluted with the thermal transport function $g_{therm}(t)$ obtained in this way, a curve very precisely matched to the cerebrovenous thermal dilution curve according to FIG. 3 results, as is shown by the solid line.

In order to determine the cerebral blood flow and the intracerebral blood volume, the values obtained for the transit times $mtt_{therm}$ and $mtt_{ICG}$ need only be put into equations (1) and (2).

I claim:

1. A process for determining cerebral blood flow CBF, and intracerebral blood volume ICBV, after injection in a patient's bloodstream of a predefined quantity of a double indicator, and arterial and venous measurement of indicator dilution curves resulting in the bloodstream, whereby a dye solution differing in temperature from body temperature serves as a double indicator, in which heat or cold constitute a highly diffusible indicator component, and dye constitutes an intravascular indicator component, comprising the steps of:

determining a distribution coefficient $\lambda_{therm}$ of the highly diffusible indicator component therm between blood and cerebral tissue;

determining a mean transit time $mtt_{therm}$ of the highly diffusible indicator component therm through the brain;

determining a mean transit time $mtt_{ICG}$ of the intravascular indicator component ICG;

calculating cerebral blood flow CBF from a ratio of the distribution coefficient $\lambda_{therm}$ of the highly diffusible indicator component therm between blood and cerebral tissue and a mean transit time $mtt_{therm}$ of the highly diffusible indicator component therm through the brain; and calculating intracerebral blood volume ICBV from a product of cerebral blood flow CBF and a mean transit time $mtt_{ICG}$ of the intravascular indicator component ICG.

2. A process according to claim 1, wherein the mean transit times $mtt_{ICG}$ and $mtt_{therm}$ are determined from transcerebral transport functions of two indicators $g_{therm}(t)$ or $g_{IGC}(t)$ respectively, whereby the mean transit times generally correspond to a first moment of transport functions according to a relation $$mtt = \frac{\int_0^\infty g(t) \cdot dt}{\int_0^\infty g(t) dt}$$

and the transport functions g(t) are determined by deconvolution of the measured arterial a(t) and cerebrovenous v(t) indicator curves of a convolution integral $$v(t) = \int_0^\infty g(t-u)a(u)du$$

3. A process according to claim 2, wherein the transport functions g(t) are determined from the measured arterial a(t) and cerebrovenous v(t) indicator curves by an iterative, non-linear matching process in which, by predefining a model function which describes the basic progress of the transport functions g(t), parameters of the model function being varied according to a process of the smallest squares until a difference between the measured cerebrovenous indicator curve v(t) and the convolution result of the measured arterial indicator curve a(t) is minimized according to a relation $$\left[ v(t) - \int_0^\infty g(t-u)a(u)du \right]^2 = \min$$

4. A process according to claim 3, wherein a logarithmic normal distribution in a form of $$g_{IGC}(t) = g_{\log nor}(t, mtt, \sigma) = \frac{1}{\sqrt{2\pi}\sigma t} \cdot e^{-\frac{\left(\ln\frac{t}{mtt} + \frac{\sigma^2}{2}\right)^2}{2\sigma^2}}$$

is selected as a model function for an intravascular dye transport functions $g_{ICG}(t)$, whereby parameters to be varied are constituted by the median transit time mtt of the dye solution ICG and by relative dispersion σ.

5. A process according to claim 4, wherein a model function for two compartments with differing rates of blood flow is modified by a sum of two logarithmic normal distributions in a form of $$g_{IGC}(t) = \alpha_{ICG} \cdot g_{log\ nor\ 1}(t, mtt_1, \sigma_1)$$
$$+ (1-\alpha_{ICG}) \cdot g_{log\ nor\ 2}(t, mtt_2, \sigma_2).$$

6. A process according to claim 4, wherein the transport function $g_{therm}(t)$ of the highly diffusible indicator component therm, by convolution of the transport function $g_{ICG}(t)$ of the intravascular indicator component ICG, is folded with a portion, describing a micro circulation $g_{mikro}(t)$, of a transport process of the highly diffusible indicator component therm in a form of $$g_{therm}(t) = G_{ICG}(t) * g_{mikro}(t)$$

whereby operator "*" corresponds to a convolution integral; and wherein for the transport function of the micro circulation, as a model function, an exponential function in a form of $$g_{mikro}(t) = mtt_{mikro}\ e^{-\dfrac{t}{mtt_{mikro}}}$$

is selected, in which mean transit time $mtt_{mikro}$ of the micro circulation is contained as a variable parameter.

7. A process according to claim 6, wherein the model function for two compartments with different blood flow is modified by a sum of two exponential functions in a form of $$g_{mikro}(t) = \alpha_{mikro} \cdot mtt_{mikro\ 1}\ e^{-\dfrac{t}{mtt_{mikro\ 1}}} +$$
$$(1-\alpha_{mikro}) \cdot mtt_{mikro\ 2}\ e^{-\dfrac{t}{mtt_{mikro\ 2}}}$$

8. A device for determining cerebral blood flow CBF, and intracerebral blood volume ICBV, after injection into a patient's bloodstream of a predefined quantity of a double indicator, and arterial and venous measurement of indicator dilution curves resulting in the bloodstream, comprising: combined fibre-optic thermistor catheters as measuring sensors for separate measuring of dilution curves of an intravascular indicator component of dye and a highly diffusible indicator component from cold or heat, therm; one of the measuring sensors being arrangeable in a central artery in front of a brain and another measuring sensor being arrangeable in a central vein behind the brain, and a computer to which the measuring sensors are connected, the computer being controlled in such a way that from measuring values of the dilution curves cerebral blood flow CBF is calculated from a ratio of a distribution coefficient $\lambda_{therm}$ of the highly diffusible indicator component therm between blood and cerebral tissue and a mean transit time $mtt_{therm}$ of the highly diffusible indicator component therm through the brain, and that intracerebral blood volume ICBV is calculated from a product of cerebral blood flow CBF and mean transit time $mtt_{ICG}$ of a intravascular indicator component ICG.

9. A device according to claim 8, wherein the computer is programmed to determine the mean transit times $mtt_{ICG}$ and $mtt_{therm}$ from cerebral transport functions of two indicators $g_{therm}(t)$ or $g_{IGC}(t)$ respectively, whereby the mean transit times generally correspond to a first moment of the transport functions according to a relation $$mtt = \dfrac{\int_0^\infty g(t) \cdot t\, dt}{\int_0^\infty g(t)\, dt}$$

and the transport functions g(t) are determined by deconvolution of measured arterial a(t) and cerebrovenous v(t) indicator curves of a convolution integral $$v(t) = \int_0^\infty g(t-u) a(u)\, du$$

10. A device according to claim 9, wherein the computer is programmed to determine the transport function g(t) from the measured arterial a(t) and cerebrovenous v(t) indicator curves by an iterative, non-linear matching process in which, by predefining a model function describing a basic progress of transport functions g(t), parameters of the model function are varied according to a process of smallest squares until a difference between the measured cerebrovenous indicator curve v(t) and a convolution result of the measured arterial indicator curve a(t) is minimized according to a relation $$\left[ v(t) - \int_0^\infty g(t-u) a(u)\, du \right]^2 = \min$$

11. A device according to claim 10, wherein a logarithmic normal distribution in the form of $$g_{IGC}(t) = g_{log\ nor}(t, mtt, \sigma) = \dfrac{1}{\sqrt{2\pi\sigma t}} \cdot e^{-\dfrac{\left(ln\dfrac{t}{mit} + \dfrac{\sigma^2}{2}\right)^2}{2\sigma^2}}$$

is selected as a model function for the intravascular dye transport function $g_{ICG}(t)$, whereby the parameters to be varied are constituted by the mean transit time mtt of the dye solution ICG and by relative dispersion $\sigma$.

12. A device according to claim 11, wherein the model function for two compartments with differing rates of blood flow is modified by a sum of two logarithmic normal distributions in a form of $$g_{IGC}(t) = \alpha_{ICG} \cdot g_{log\ nor\ 1}(t, mtt_1, \sigma)$$
$$+ (1-\alpha_{ICG}) g_{log\ nor\ 2}(t, mtt_2, \sigma_2).$$

13. A device according to claim 11, wherein the transport function $g_{therm}(t)$ of the highly diffusible indicator component therm, by convolution of the previously determined transport function $g_{ICG}(t)$ of the intravascular indicator component ICG, is folded with a portion, describing a micro circulation $g_{mikro}(t)$, of the transport process of the highly diffusible indicator component therm in a form of $$g_{therm}(t)\ g_{ICG}(t) * g_{mikro}(t)$$

whereby operator "*" corresponds to the convolution integral; and for a transport function of the micro circulation, as a model function, an exponential function in a form of $$g_{mikro}(t) = mtt_{mikro}\, e^{-\frac{t}{mtt_{mikro}}}$$

is selected, in which a mean transit time $mtt_{mikro}$ of the micro circulation is contained as a variable parameter.

14. A device according to claim 13, wherein a model function for two compartments with different blood flow is modified by a sum of two exponential functions in a form of $$g_{mikro}(t) = \alpha_{mikro} \cdot mtt_{mikro\,1}\, e^{-\frac{t}{mtt_{mikro\,1}}} + (1 - \alpha_{mikro}) \cdot mtt_{mikro\,2}\, e^{-\frac{t}{mtt_{mikro\,2}}}$$

* * * * *